United States Patent
Bratton et al.

[11] Patent Number: 5,867,999
[45] Date of Patent: Feb. 9, 1999

[54] EVAPORATIVE COOLING BAND DEVICE

[76] Inventors: Bert Bratton, 1850 Gause, Suite 303, Slidell, La. 70461; Milton N. Dudenhefer, III, 113 Anita Pl., Slidell, La. 70458

[21] Appl. No.: 567,113

[22] Filed: Dec. 4, 1995

[51] Int. Cl.⁶ .................................................. F25D 7/00
[52] U.S. Cl. .................. 62/259.3; 62/259.4; 62/304; 62/314; 62/316; 454/370; 607/96; 607/107; 165/46
[58] Field of Search ............................. 62/304, 316, 314, 62/259.3, 259.4; 454/370; 607/96, 107; 165/46, 47

[56] References Cited

U.S. PATENT DOCUMENTS

| | | | |
|---|---|---|---|
| 2,206,481 | 7/1940 | Luchs et al. | 165/46 |
| 2,416,788 | 3/1947 | Andrews | 607/107 |
| 2,460,269 | 2/1949 | Appeldoorn | 165/46 |
| 2,540,547 | 2/1951 | Rodert | 165/46 |
| 3,279,201 | 10/1966 | Wortz et al. | 62/259.3 |
| 4,138,743 | 2/1979 | Elkins et al. | |
| 4,483,021 | 11/1984 | McCall | |
| 4,951,665 | 8/1990 | Schneider | 165/46 |
| 5,146,757 | 9/1992 | Dearing | |
| 5,193,347 | 3/1993 | Apisdorf | |
| 5,217,408 | 6/1993 | Kaine | 62/259.3 |
| 5,327,585 | 7/1994 | Karlan | |
| 5,342,411 | 8/1994 | Maxted et al. | |
| 5,353,605 | 10/1994 | Naaman | 62/259.3 |

FOREIGN PATENT DOCUMENTS 573514  2/1958  Italy ...................................... 62/259.3

*Primary Examiner*—John K. Ford

[57] ABSTRACT

An evaporative cooling band device adapted to be positioned upon a user's body, the apparatus comprising: a horizontally disposed band formed in a circular configuration, the band including a hose with a plurality of apertures and a moisture absorbing covering, the hose having two free ends, a Y-shaped tube connector being coupled to the free ends of the hose.

5 Claims, 3 Drawing Sheets

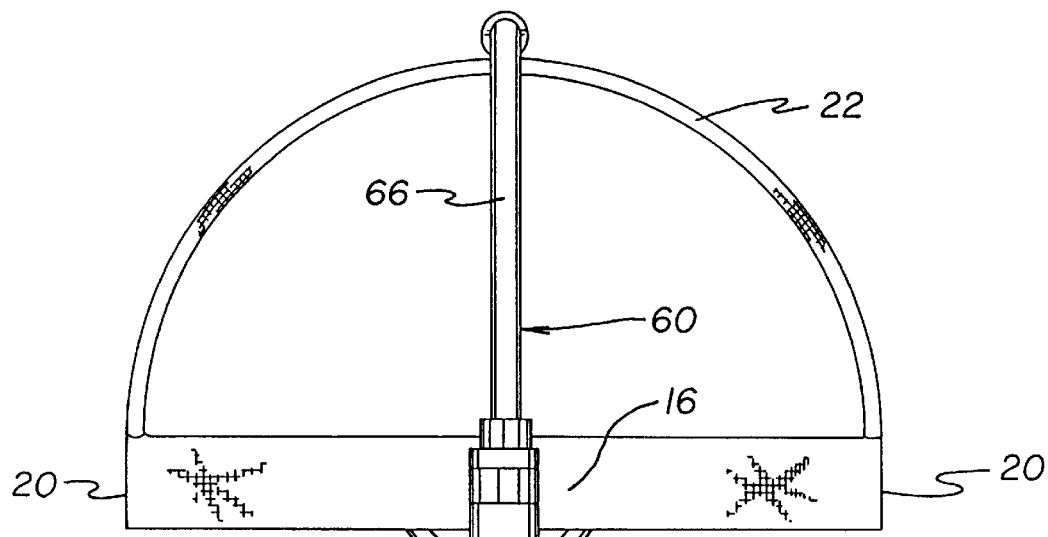
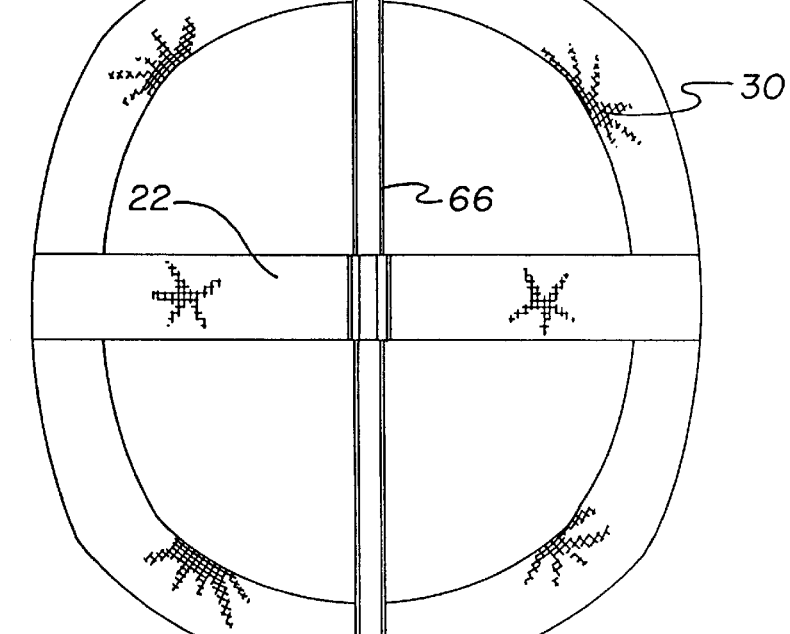
FIG.3
FIG.4

# EVAPORATIVE COOLING BAND DEVICE

BACKGROUND OF THE INVENTION

1. Field of the Invention

The present invention relates to an evaporative cooling band device and more particularly pertains to evaporatively cooling a user's body by activating the air suction device of the assembly.

2. Description of the Prior Art

The use of head cooling devices is known in the prior art. More specifically, head cooling devices heretofore devised and utilized for the purpose of cooling the heads of users by a variety of different methods are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 5,342,411 to Maxted a scalp cooling device.

U.S. Pat. No. 5,327,585 to Karlan discloses a cool cap.

U.S. Pat. No. 5,193,347 to Apisdorf discloses a helmet-mounted air system for personal comfort.

U.S. Pat. No. 5,146,757 to Dearing discloses a helmet cooling system.

U.S. Pat. No. 4,483,021 to McCall discloses a thermoelectric cooled head gear.

Lastly, U.S. Pat. No. 4,138,743 to Elkins discloses a liquid cooled helmet.

In this respect, the evaporative cooling band device according to the present invention substantially departs from the conventional concepts and designs of the prior art, and in doing so provides an apparatus primarily developed for the purpose of evaporatively cooling a user's body by activating the air suction device of the assembly.

Therefore, it can be appreciated that there exists a continuing need for a new and improved evaporative cooling band device which can be used for evaporatively cooling a user's body by activating the air suction device of the assembly. In this regard, the present invention substantially fulfills this need.

SUMMARY OF THE INVENTION

In view of the foregoing disadvantages inherent in the known types of head cooling devices now present in the prior art, the present invention provides an improved evaporative cooling band device. As such, the general purpose of the present invention, which will be described subsequently in greater detail, is to provide a new and improved evaporative cooling band device and method which has all the advantages of the prior art and none of the disadvantages.

To attain this, the present invention essentially comprises a new and improved evaporative cooling band device adapted to be positioned upon the scalp of a user, the apparatus comprising, in combination: a new and improved evaporative cooling band device adapted to be positioned upon the scalp of a user, the apparatus comprising, in combination: a horizontally disposed band formed in a circular configuration, the horizontally disposed band having a width of about one inch and adapted to be positioned around the scalp of a user, the horizontally disposed band having a front region, a rear region and two side regions, a vertically disposed band formed in a semi-circular configuration and coupled to each side region of the horizontally disposed band, the horizontally disposed band including a hollow rubber hose with a plurality of apertures, each band including a cotton covering, the hose of the horizontally disposed band having two ends operatively coupled to a main hose, the main hose having a free end, an air suction device including an air flow regulator and a spout, the spout adapted to be coupled to the free end of the main hose, in an operative orientation the air suction device causing air to be suctioned from the band and hose thereby evaporatively cooling a user's scalp; and a pivotable light comprising an electrically powered L-shaped illumination device with a frontwardly projecting lens and a rearwardly projecting axle, a bearing being coupled to the front region of the horizontally disposed band, the axle being positioned within the bearing thereby permitting pivotable movement of the illumination device to direct a beam of light in a desired direction, an electrical cord having a flexible rearward portion with a first end terminating in an electrical plug, the electrical plug adapted to be coupled within an electrical outlet, the electrical cord having a rigid frontward portion, the rigid frontward portion being coupled to the rear portion of the horizontally disposed band and an upper extent of the vertically disposed band, a second end of the cord being electrically coupled to the illumination device.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved evaporative cooling band device which has all of the advantages of the prior art head cooling devices and none of the disadvantages.

It is another object of the present invention to provide a new and improved evaporative cooling band device which may be easily and efficiently manufactured and marketed.

It is further object of the present invention to provide a new and improved evaporative cooling band device which is of durable and reliable constructions.

An even further object of the present invention is to provide a new and improved evaporative cooling band device which is susceptible of a low cost of manufacture with regard to both materials and labor, and which accordingly is then susceptible of low prices of sale to the consuming public, thereby making such evaporative cooling band device economically available to the buying public.

Still yet another object of the present invention is to provide a new and improved evaporative cooling band device which provides in the apparatuses and methods of the prior art some of the advantages thereof, while simultaneously overcoming some of the disadvantages normally associated therewith.

Still another object of the present invention is to evaporatively cooling a user's body by activating the air suction device of the assembly.

Lastly, it is an object of the present invention to provide a new and improved evaporative cooling band device adapted to be positioned upon a user's body, the apparatus comprising: a horizontally disposed band formed in a circular configuration, the band including a hose with a plurality of apertures and a moisture absorbing covering, the hose having two free ends, a Y-shaped tube connector being coupled to the free ends of the hose.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a front perspective view of the evaporative cooling band device shown in FIG. 1.

FIG. 4 is a top plan view of the evaporative cooling band device.

The same reference numerals refer to the same parts through the various Figures.

DESCRIPTION OF THE PREFERRED EMBODIMENT

Figure 1:
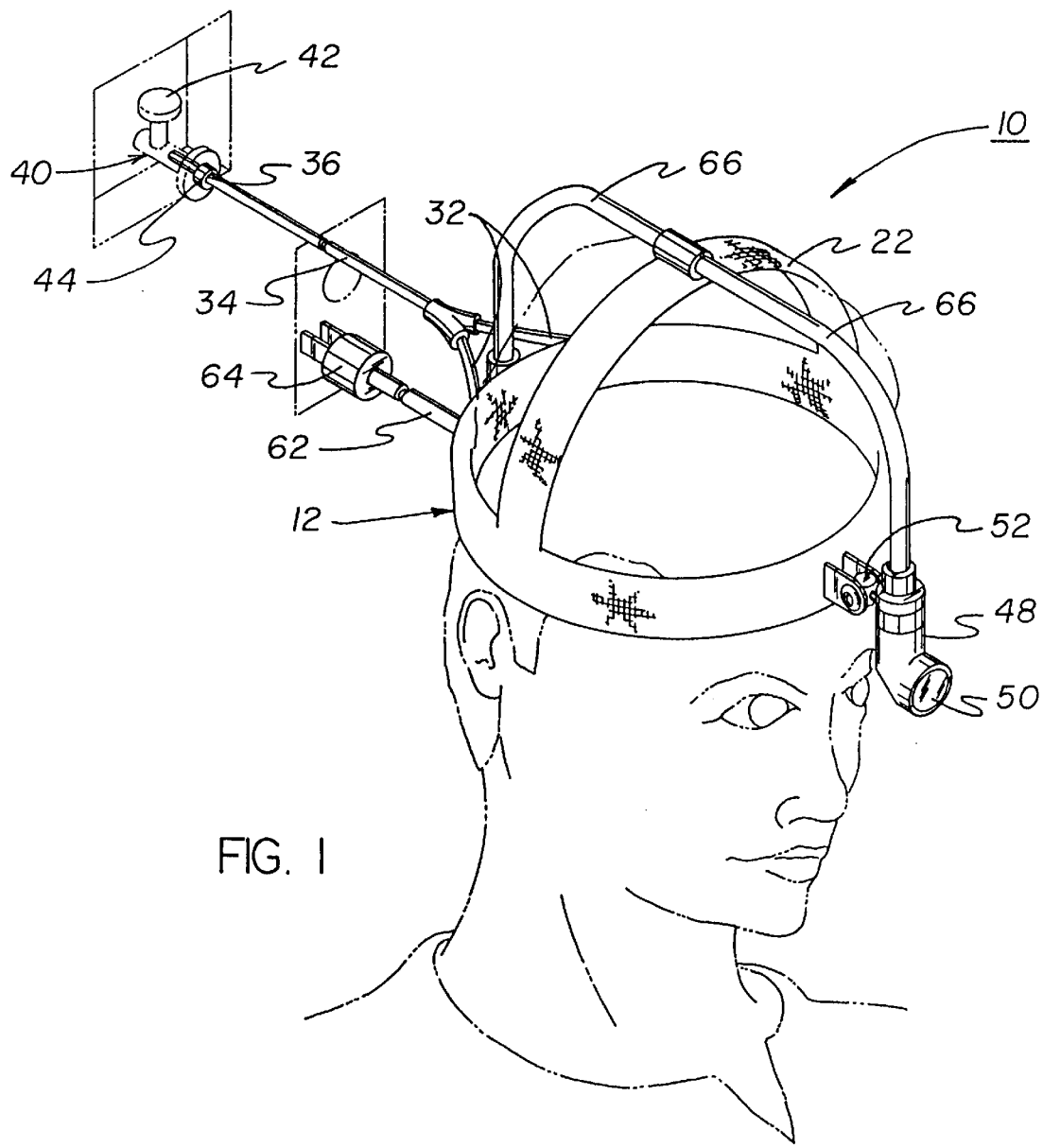
FIG. 1 is a perspective view of the preferred embodiment of the evaporative cooling band device constructed in accordance with the principles of the present invention.

With reference now to the drawings, and in particular to FIG. 1 thereof, the preferred embodiment of the new and improved evaporative cooling band device embodying the principles and concepts of the present invention and generally designated by the reference numeral 10 will be described.

The present invention, the evaporative cooling band device 10 is comprised of a plurality of components. Such components in their broadest context include a horizontally disposed band 12, a vertically disposed band 22, a pivotable light 48 and an electric cord 62. Such components are individually configured and correlated with respect to each other so as to attain the desired objective.

The new and improved evaporative cooling band device is adapted to be positioned upon the scalp of a user in the preferred embodiment. The apparatus is particularly useful to surgeons when performing surgery in an operating room. Operating rooms are typically cooled to between 55 and 60 degrees when surgery is being performed. This temperature is uncomfortably cool to personnel working in the operating room. The present invention serves to keep surgeons cooler than they ordinarily would be given the temperature in the operating room. This permits raising of the temperature in the operating room to a more comfortable level. Alternative embodiments of the apparatus are described below. In such embodiments the apparatus is shaped and sized to be placed around the waist, leg, neck or arm of a user.

Figure 2:
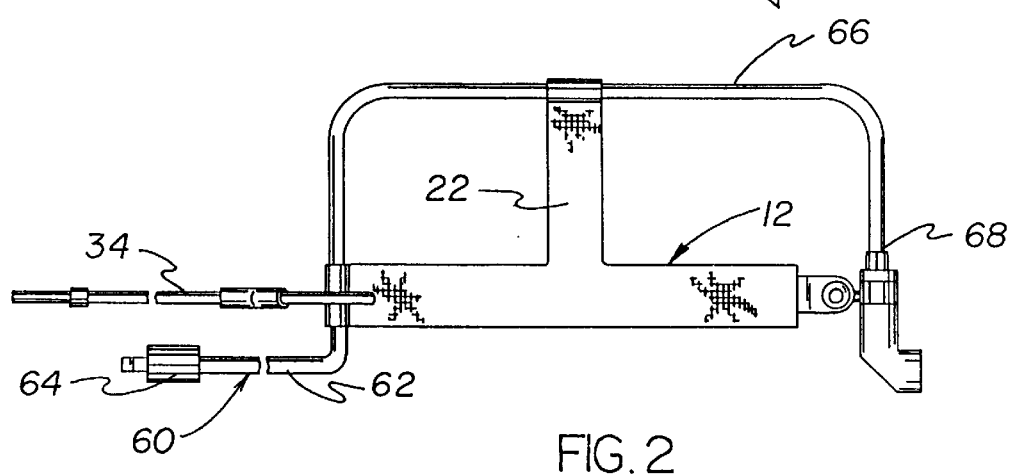
FIG. 2 is a side perspective view of the evaporative cooling band device shown in FIG. 1.

More specifically, a horizontally disposed band 12 is formed in a circular configuration. The horizontally disposed band has a width of about one inch and is adapted to be positioned around the scalp of a user. The band is formed of a semi-rigid material thereby permitting flexibility to contour to the size of an individual user's head. The horizontally disposed band has a front region 16, a rear region 18 and two side regions 20. The front region is positioned across a user's forehead in the operative orientation. A vertically disposed band 22 is formed in a semi-circular configuration and coupled to each side region 20 of the horizontally, disposed band. When the apparatus is positioned upon the user's head the vertically disposed band is positioned adjacent to the user's ears. Note FIGS. 1 and 2.

Figure 5:
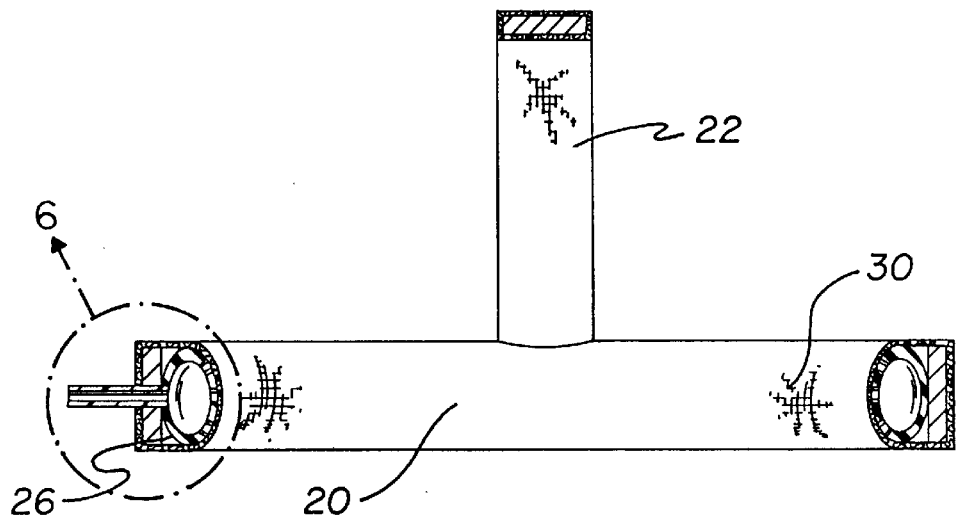
FIG. 5 is a cross sectional view of the apparatus taken along section line 5—5 of FIG. 4.
Figure 6:
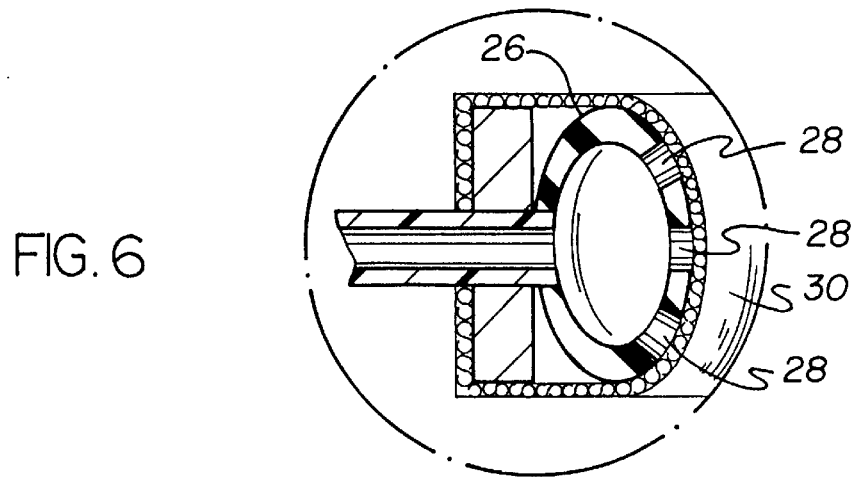
FIG. 6 is a cross sectional view of the apparatus taken along section line 6 of FIG. 5.

Each band includes a hollow rubber hose 26 with a plurality of apertures 28. Each band includes a cotton covering 30. Cotton is utilized to provide an ideal surface for absorption of perspiration emanating from the user. In the operative orientation the absorbed perspiration is quickly evaporated by the action of the air suction device. In alternative embodiments of the apparatus other types of moisture absorbing materials such as cloth and various synthetic materials are utilized to absorb perspiration. Note FIGS. 5 and 6.

The hose in the horizontally disposed band has two ends 32 operatively coupled-to the hose in the horizontally disposed band. The hose in the horizontally disposed band has two ends 32 operatively coupled to an elongated main hose 34. The elongated main hose is between twenty and fifty feet in length and includes a free end 36. The long length permits users to operate long distances from a suction device. Note FIGS. 3 and 4.

The apparatus includes an air suction device which has an air flow regulator 42 and a spout 44. The spout is adapted to be coupled to the free end of the main hose. The air flow regulator permits the user to control the rate of air flow through the apparatus. An increased air flow rate causes more evaporative cooling to take place. In alternative embodiments of the apparatus an air suction device is not included. In such embodiments the free end of the main hose is adapted to be coupled to the air suction devices routinely found in medical operating rooms. In the operative orientation the air suction device causes air to be suctioned from the bands and hoses, thereby evaporatively cooling a user's scalp. Note FIGS. 1 and 2.

Figure 7:
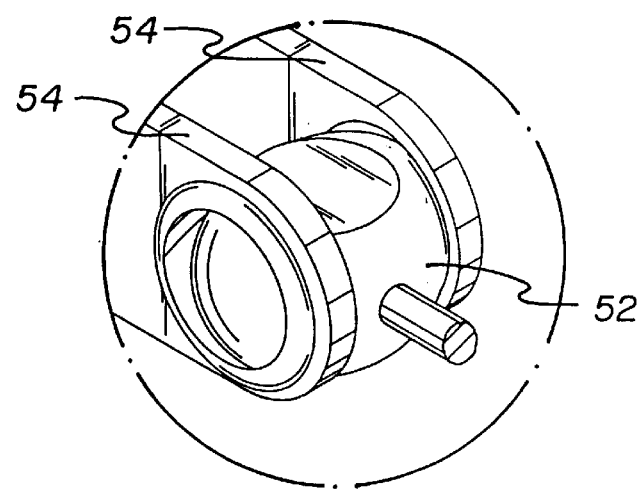
FIG. 7 is a cross sectional view of the apparatus taken along section line 7 of FIG. 4.

A pivotable light 48 comprises an electrically powered L-shaped illumination device with a frontwardly projecting lens 50 and a rearwardly projecting axle 52. A bearing 54 is coupled to the front region of the horizontally disposed band. The axle 52 is positioned within the bearing 54 thereby permitting pivotable movement of the illumination device to direct a beam of light in a desired direction. This is a particularly useful feature when the apparatus is being utilized by a surgeon while performing surgery. The pivotal feature of the device allows direction of light at a plurality of different angles. It permits a surgeon to direct light specifically to the area being worked on. In alternative embodiments of the apparatus the light is not included. In further alternative embodiments of the apparatus the light is included but is battery operated as opposed to being AC-electrically powered. Note FIGS. 1 and 7.

An elongated electrical cord 60 has a flexible rearward portion 62 with a first end terminating in an electrical plug 64. The electrical plug is adapted to be coupled within an electrical outlet. The electrical cord has a rigid frontward portion 66. The rigid frontward portion 66 is coupled to the rear portion of the horizontally disposed band and an upper extent of the vertically disposed band. A second end 68 of the cord is electrically coupled to the illumination device. The cord is between twenty and fifty feet in length to allow the user a great degree of maneuverability when utilizing the apparatus. Note FIGS. 1, 2 and 4.

Several alternative embodiments of the apparatus are available. In such embodiments the apparatus does not include a pivotable light or electrical cord. In a first alternate embodiment the apparatus is fabricated of disposable materials and adapted to be coupled to a commercially available pivotable light. In a second alternate embodiment the apparatus is fabricated of reusable materials and adapted to be coupled to a commercially available pivotable light. The first and second alternate embodiments utilize VELCRO or snap devices to couple the apparatus to the pivotable light.

Other alternative embodiments of the apparatus do not include a vertically disposed band and are shaped and sized to be placed around the waist, leg, neck or arm of a user. Such embodiments may be positioned underneath or around a user's clothing. The waist adapted apparatus has a diameter of between about twelve and twenty four inches. The leg and neck adapted apparatuses have a diameter of between about five and ten inches. The arm adapted apparatus has a diameter of between about two and four inches.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An evaporative cooling band device adapted to be positioned upon a user's body, the device comprising:

a horizontally disposed band formed in a circular configuration, the band including a hose with a plurality of apertures and a moisture absorbing covering, the hose having two free ends, a Y-shaped tube connector being coupled to the free ends of the hose.

2. The evaporative cooling band device as set forth in claim 1 and further including:

a main hose having a first free end and a second end couplable to the Y-shaped tube connector; and an air suction device including an air flow regulator and a spout, the spout adapted to be coupled to the free end of the main hose, in an operative orientation the air suction device causing air to be suctioned from the band and hose thereby evaporatively cooling a user's body.

3. The evaporative cooling band device as set forth in claim 1 and further including a vertically disposed band formed in a semi-circular configuration and coupled to the horizontally disposed band.

4. The evaporative cooling band device as set forth in claim 3 and further including:

a pivotable light comprising an electrically powered L-shaped illumination device with a frontwardly projecting lens and a rearwardly projecting axle, a bearing being coupled to the horizontally disposed band, the axle being positioned within the bearing thereby permitting pivotable movement of the illumination device to direct a beam of light in a desired direction, an electrical cord having a flexible rearward portion with a first end terminating in an electrical plug, the electrical plug adapted to be coupled within an electrical outlet, the electrical cord having a rigid frontward portion, the rigid frontward portion being coupled to the horizontally disposed band and an upper extent of the vertically disposed band, a second end of the cord being electrically coupled to the illumination device.

5. A new and improved evaporative cooling band device adapted to be positioned upon the scalp of a user, the apparatus comprising, in combination:

a horizontally disposed band formed in a circular configuration, the horizontally disposed band having a width of about one inch and adapted to be positioned around the scalp of a user, the horizontally disposed band having a front region, a rear region and two side regions, a vertically disposed band formed in a semi-circular configuration and coupled to each side region of the horizontally disposed band, the horizontally disposed band including a hollow rubber hose with a plurality of apertures, each band including a cotton covering, the hose of the horizontally disposed band having two ends operatively coupled to a main hose, the main hose having a free end, an air suction device including an air flow regulator and a spout, the spout adapted to be coupled to the free end of the main hose, in an operative orientation the air suction device causing air to be suctioned from the band and hose thereby evaporatively cooling a user's scalp; and a pivotable light comprising an electrically powered L-shaped illumination device with a frontwardly projecting lens and a rearwardly projecting axle, a bearing being coupled to the front region of the horizontally disposed band, the axle being positioned within the bearing thereby permitting pivotable movement of the illumination device to direct a beam of light in a desired direction, an electrical cord having a flexible rearward portion with a first end terminating in an electrical plug, the electrical plug adapted to be coupled within an electrical outlet, the electrical cord having a rigid frontward portion, the rigid frontward portion being coupled to the rear portion of the horizontally disposed band and an upper extent of the vertically disposed band, a second end of the cord being electrically coupled to the illumination device.

* * * * *